United States Patent [19]
Loosemore

[11] Patent Number: 6,107,344
[45] Date of Patent: Aug. 22, 2000

[54] AQUEOUS GERMICIDAL FILM FORMING COMPOSITION FOR APPLYING TO TEATS OF DAIRY COWS

[75] Inventor: Michael J. Loosemore, Auburn, Mass.

[73] Assignee: Webco Chemical Corporation, Dudley, Mass.

[21] Appl. No.: 09/249,995

[22] Filed: Feb. 16, 1999

[51] Int. Cl.$^7$ ...................................... A61K 31/74
[52] U.S. Cl. ........................... 514/635; 428/405; 428/438; 428/78.02; 428/78.03; 428/78.07; 514/772.3; 514/772.7; 514/772.5
[58] Field of Search ..................................... 424/405, 438, 424/78.02, 78.03, 78.07; 514/772.3, 772.5, 772.7, 635

[56] References Cited

U.S. PATENT DOCUMENTS

| | | | |
|---|---|---|---|
| 5,142,010 | 8/1992 | Olstein | 526/248 |
| 5,529,770 | 6/1996 | McKinzie et al. | 424/78.24 |

*Primary Examiner*—Frederick Krass
*Attorney, Agent, or Firm*—Terry M. Crellin

[57] ABSTRACT

Aqueous film forming compositions are disclosed that are to be applied to the teats of dairy animals to form a protective film on the teats. The protective film may be applied as a dip or spray. The compositions comprise a polyethylene glycol-lanolin complex and an amide condensation product of monoethanolamine and an organic acid having a carbon chain length of from 2 to 4. The compositions can further include xanthan and a germicidal agent.

17 Claims, No Drawings

AQUEOUS GERMICIDAL FILM FORMING COMPOSITION FOR APPLYING TO TEATS OF DAIRY COWS

BACKGROUND OF THE INVENTION

1. Field of the Invention

This invention relates to new aqueous germicidal compositions useful for reduction or prevention of environmental and contagious mastitis in dairy animals. In particular, the invention relates to aqueous compositions containing antimicrobial agents and film forming agents used to form a protective, germicidal film on the teats and the ends of the teats of dairy animals such that the animals' skin is physically protected from pathogenic organisms and extraneous material.

2. State of the Art

Various compositions are available to dairy operators for the purpose of germicidal disinfecting of the skin surfaces on the teats of dairy cows. In addition to providing a germicidal disinfectant, there are compositions available that establish a barrier film such that the disinfected teat skin is physically protected from the unhindered reintroduction of pathogens back onto the teat skin surface. Various of the film forming compositions will also form a plug of material at the opening of the mammary sphincter to provide protection from the introduction of pathogenic organisms into the mammary canal. The control of pathogenic organisms on the teat skin of dairy cows is a major goal of the dairy industry. Contact with the bovine mammary gland by a pathogenic microorganism, usually bacteria but occasionally yeast or fungi, can result in the disease of mastitis. Mastitis is a serious infection which can in severe cases, cause death to the dairy cow and even in much milder cases can result in long term damage to the cow, loss of milk production for the dairy farmer and overall an unacceptable increase in costs to the farmer.

Mastitis is indeed widely considered to be the single most costly disease in the dairy industry. Efforts to control the presence of infectious agents date back to the early 1900's but the success of these efforts was limited by the unavailability of effective germicidal agents. The incidence of mastitis has decreased over the last twenty-five years due to the realization that proper hygiene, particularly with regard to the udder and teat surfaces of the cow is very important and due to the widespread acceptance of the practice of dipping the cows teats in a germicidal agent after milking.

Modern vacuum milking machines have perhaps made teat dipping more critical. Vacuum milking causes a relaxation of the sphincter muscle at the end of the teat canal resulting in an open canal which may require several minutes to hours to contract and close. This open period proffers a direct access route, a veritable highway for microbes, leading to the mammary gland. Dipping the teat in a disinfectant immediately after milking has been shown to be an economical and effective measure in helping to reduce the incidence of mastitis infection. Many disinfectant agents have been used in teat dips, among them: iodine, chlorine, chlorine dioxide, chlorhexidine, fatty acids, anionic surfactants and quaternary ammonium compounds.

These disinfectant agents are generally useful for helping to reduce the bacterial population on the teat skin. Mastitis still persists as the significant dairy cow disease which indicates that the current products do not address all areas of concern. It is an ironic twist that some of the available teat dip agents, notably iodine and chlorine, may in fact, contribute to the mastitis problem by causing irritation of the teat skin, thus providing an opportunistic site which promotes infection. Many available teat dip formulations attempt to combat this potential for irritation by incorporating emollient agents in an effort to soothe the skin. Additionally, some of the more powerful disinfectants, chlorine for example, can be particularly noxious for the user as well. Others such as fatty acids and anionic surfactants are not broad enough in their antibacterial spectrum to provide complete protection.

Regardless of which germicidal agent is employed or how it is formulated, the ultimate objective of teat sanitation is to minimize teat contamination for as long as possible. It is on this point that conventional teat dips fail. Once germicidal activity of the teat dip ceases, there is no control of environmental pathogens which may be encountered by the teat skin and open mammary canal. Recent product developments have sought to provide better environmental pathogen protection by bringing forth new teat dips referred to as barrier dips. These products seek to provide an antimicrobial agent as well as a coating for the teat skin and a plugging of the open teat canal.

Efforts have been made to protect cows during the vulnerable post milking period by attempting to seal the teat skin and sphincter opening with a barrier type teat dip. Many approaches to preparing barrier teat dips have been tried with varying degrees of success. Barrier dips have heretofore been composed of numerous film forming agents with and without the incorporation of antimicrobials into the compositions. Teat dip compositions containing cellulosic film formers are disclosed in U.S. Pat. Nos. 4,330,531 and 4,376,787. U.S. Pat. No. 4,022,199 discloses a teat dip composition comprising solvent gum and water mixtures. Synthetic polymers are disclosed as film forming agents in U.S. Pat. No. 5,017,369. The use of latex as a film forming agent is disclosed in U.S. Pat. No. 4,113,854, and the use of fats or oils in teat dip compositions is illustrated in U.S. Pat. No. 3,222,252.

None of the present approaches has been found to be entirely satisfactory. Some film forming agents, such as cellulose form dry easily cracked coatings that could easily be breached by pathogenic organisms. In other cases the germicides, solvents, or the film forming agents or polymers themselves can be potentially irritating. Still other compositions such as oil based products can be too difficult to remove even with a detergent product and some of the polymer films can be brittle, insoluble and difficult to remove. It can be seen that there is still the need for an improved, durable, adherent, flexible but readily removable film forming barrier teat dip composition that is non-irritating to the teat skin and compatible with a number of effective germicidal agents.

OBJECTIVES AND BRIEF DESCRIPTION OF THE INVENTION

A principal objective of the present invention is to provide an improved, effective, film forming germicidal barrier teat dip that is durable, flexible, non-irritating, and further is composed of skin conditioners, is non-greasy and is readily and completely removable prior to milking.

Another objective of the present invention is to provide such an improved teat dip composition which forms a protective film on the entire teat of the animal as well as at the opening of the mammary canal.

In accordance with the present invention, an improved teat dip composition has been found that utilizes the properties of a unique blending of humectant, emollient and viscosity control agents to produce a particularly advantageous, effective, germicidal, aqueous barrier that is comprised of skin conditioners, is non-greasy, is durable, is flexible, is non-irritating and is readily and completely removable prior to milking. It has been discovered that the unique blending of certain organic materials otherwise recognized as emollients and thickeners can be employed to provide an unexpected and surprisingly long lived, flexible, adherent, anti-microbial film which can be applied to the teats of dairy animals to produce a protective, germicidal barrier. The method of application is herein referred to as teat dipping, but it is recognized that other methods of application, such as spraying or brushing, can be utilized where appropriate and will be familiar to those experienced in the art.

The formulations of this invention provide a durable, flexible and adherent film barrier which can be easily removed when desired by simple washing of the cow teats prior to milking. The ingredients of this invention are non-toxic and non-irritating. The incorporation of a germicidal agent into the film formed by this invention provides a long lasting germicidal active teat skin covering during that vulnerable period between milkings.

It has been found that an exceptionally advantageous, novel, barrier composition can be produced by careful blending of polyethylene glycol modified lanolin (peg-lanolin) with the amide condensation product of monoethanolamine and certain short carbon chain organic acids and xanthan in an aqueous base. The novel barrier composition forms a film with desirable properties and is compatible with all germicidal agents that can be incorporated in water based compositions. The properties of the resultant film have been found to be dependent upon the relative ratios of the peg-lanolin to the amide condensation product to the xanthan. Advantageously, the composition of the present invention comprises about 0.1% to 5% peg-lanolin by weight, about 0.4% to 20% by weight of the amide condensation product and about 0.05% to 3% by weight germicidal agent.

DETAILED DESCRIPTION OF THE PREFERRED EMBODIMENTS

As mentioned previously, the germicidal barrier composition of the present invention comprises a unique, novel blend of a humectant, an emollient and a viscosity control agent. In particular, it has been found that very effective barrier compositions are obtained by blending polyethylene glycol modified lanolin (peg lanolin), an amide condensation product of monoethanolamine and xanthan in an aqueous base. These novel compositions are compatible with almost any germicidal agent that can be incorporated in water based compositions. The novel compositions advantageously form very effective barrier films on the teats of dairy animals, but the barrier films in turn can be readily washed from the teats prior to milking of the animal.

The polyethylene glycol-lanolin complex used in the composition of the present invention is a member of the group of commercially available polyethylene glycol-lanolin complexes that differ only in respect to the relative content of the polyethylene in the complex. Particularly useful in the present invention are those polyethylene glycol-lanolin complexes designated as between polyethylene glycol 32-lanolin (peg 32 lanolin) and polyethylene glycol 75-lanolin (peg 75 lanolin). Throughout this specification and claims, whenever the polyethylene glycol-lanolin complex is referred to simply as peg lanolin, it is to be understood that any and all of the members of the group of such complexes between peg 32 lanolin and peg 75 lanolin are included, including mixtures of such complexes. The novel barrier compositions of the present invention perform substantially equal when any of the peg lanolin complexes, including mixtures thereof, in the range of peg 32 lanolin to peg 75 lanolin are incorporated into the barrier compositions.

The amide condensation products useful in the barrier compositions of the present invention are condensation products of monoethanolamine and an organic acid having a carbon chain length of between two and four. Amide condensation products of monoethanolamine and acetic acid, lactic acid and mixtures of acetic acid and lactic acid are advantageously used inasmuch as they are commercially available. These condensation products are commonly referred to as acetamide mea, lactamide mea and acetamide/lactamide mea. Throughout the present specification and claims, the general term "amide mea" is meant to include all amide condensation products of monoethanolamine and an organic acid having a carbon chain length of between two and four.

When the peg lanolin and amide mea are used individually, the resulting film that is formed was found to be completely unacceptable as a barrier film. When amide mea is used alone, there is in fact no appreciable film formation at all. Films formed by using peg lanolin alone are not flexible, but instead quite brittle, waxy and tacky. These films easily cracked. They provided absolutely no barrier protection because of the cracking of the film. It was discovered that mixtures of amide mea and peg lanolin produced thin but surprisingly non-tacky and flexible films. This was particularly the case with ratios of peg lanolin to amide mea of greater than 1:3, that is from about 1:3 to about 1:10 peg lanolin to amide mea.

Films formed of xanthan alone are completely useless as a barrier. The xanthan films were flaky and dry and easily destroyed. They provided absolutely no barrier protection. When xanthan is used in combination with peg lanolin, the resultant film was simply a deposition of the individual components. The films were not flexible but instead quite brittle and easily cracked. The films formed by the combination of xanthan and peg lanolin retained the worst features of the individual components, and this was found to be true at any and all ratios of xanthan to peg lanolin. Films formed when xanthan and amide mea are used in combination were found to be essentially the same as when xanthan is used alone. As mentioned previously, that film is completely useless as a barrier. The use of amide mea in combination with xanthan did appear to produce an improved adhesion of the xanthan film, especially when the ratio of amide mea to xanthan exceeded 2:1, but, unfortunately, the film itself was completely useless as a barrier as noted previously.

As mentioned previously, it was found that mixtures of amide mea and peg lanolin produced thin but surprisingly non-tacky and flexible film. It was further unexpectedly found that addition of xanthan to the peg lanolin and amide mea compositions resulted in films in which the thickness could be better controlled as could the tendency to drip. The resulting films formed by the compositions comprising mixtures of peg lanolin, amide mea and xanthan do not retain the brittle, cracking nature of the films formed when using peg lanolin alone or of the films using peg lanolin and xanthan in combination with each other. Nor do the films formed by the compositions containing mixtures of peg lanolin, amide mea and xanthan have the waxy, greasy nature of the peg lanolin when used alone.

The compositions containing mixtures of peg lanolin, amide mea and xanthan formed markedly improved films compared to any of the individual components. It was further unexpectedly found that the mixture of peg lanolin, amide mea and xanthan produced a barrier film having exceptional resistance to removal by environmental moisture and incidental water contact when the ratio of peg lanolin, amide mea and xanthan in the mixture is between 1:4:1 and 2:20:1, and more preferably between 1:6:1 and 2:8:1.

In addition to forming a teat barrier product that results in a flexible, protective film on the teats of dairy animals, it is advantageous to incorporate a germicidal agent in the product. It was found to be particularly advantageous to incorporate a germicidal agent or agents in the barrier film forming compositions of the present invention. The germicidal agent must be compatible with use in aqueous based compositions. Generally, any of the germicidal agents that are compatible with aqueous based compositions can be incorporated in the film forming compositions of the present invention. It has been found that chlorhexidine salts and complexes of iodine with nonionic surfactants are very effective germicidal agents that can be incorporated in the film forming compositions of the present invention.

It has also been found that it is advantageous to incorporate nonionic surfactants into the film forming compositions of the present invention. Representative nonionic surfactants that can be incorporated into the film forming compositions of the present invention include nonyl phenol ethoxylates (12 mole) and alcohol ethoxylates.

Emollients or humectants such as polyethylene glycol 200 or polyethylene glycol 400 can be added to the film forming compositions of the present invention, if desired. However, it has been found that other water soluble emollients and humectants such as glycerin and propylene glycol, while stable in the compositions of the present invention, were found to destabilize the film forming properties of such compositions.

The barrier film forming composition of the present invention may also contain buffering agents. A number of suitable buffers are available to those skilled in the art. Preferred buffering agents are citric acid in combination with its sodium salt in a ratio of about 1:2 at a total level of about 0.1 to 1.0%, preferably, 0.25 to 1.0%, and most preferred 0.5 to 1.0% by weight.

Representative examples of concentrations of the various components of the composition of the present invention are given in the following table.

| PREFERRED CONCENTRATIONS OF COMPONENTS | | |
| --- | --- | --- |
| Component | Preferred % by weight | Most Preferred % by weight |
| peg lanolin | 0.1 to 5.0 | 0.5 to 2.0 |
| amide mea | 0.4 to 20.0 | 2.0 to 8.0 |
| xanthan | 0.05 to 3.0 | 0.25 to 1.5 |
| nonionic surfactant | 1.0 to 12.0 | 2.0 to 10.0 |
| germicidal agent | 0.1 to 12.0 | 1.0 to 10.0 |
| emollients and/or humectants | 1.0 to 12.0 | 2.0 to 10.0 |
| buffering agent | 0.05 to 3.0 | 0.15 to 2.5 |
| citric acid | 0.02 to 2.0 | 0.05 to 1.6 |
| balance water | | |

Representative examples of preferred ingredients and their concentration in the composition of the present invention are given in the following table.

| PREFERRED INGREDIENTS AND CONCENTRATIONS | | |
| --- | --- | --- |
| Ingredient | Preferred % by weight | Most Preferred % by weight |
| peg 60 lanolin | 0.1 to 5.0 | 0.5 to 2.0 |
| acetamide mea | 0.4 to 20.0 | 2.0 to 8.0 |
| xanthan | 0.05 to 3.0 | 0.25 to 1.5 |
| nonyl phenol ethoxylate 12 mole | 1.0 to 12.0 | 2.0 to 10.0 |
| iodine/surfactant complex | 1.0 to 12.0 | 2.0 to 10.0 |
| polyethylene glycol 200 | 1.0 to 12.0 | 2.0 to 10.0 |
| sodium citrate | 0.05 to 1.0 | 0.1 to 0.8 |
| citric acid | 0.02 to 2.0 | 0.05 to 1.6 |
| balance water | | |

A particular preferred composition of the present invention containing (all percentages are by weight) xanthan 0.6%, peg 60 lanolin 0.9%, acetamide mea 3.7%, nonyl phenol ethoxylate 12 mole 5.0%, polyethylene glycol 200 7.0%, iodine/nonionic surfactant complex 5.0%, citric acid 0.2%, sodium citrate 0.4% and balance water was tested for germicidal efficacy against eight commonly encountered pathogens. This composition had a final pH of 5.5 and a titratable iodine content of 1.0%. The percentage kill of the eight pathogens (Staph. aureus, Strep. agalactiae, Strep. dysgalactiae, Strep. uberis, E. coli, E. aerogenes, K. pneumoniae and Pseudo. aeruginosa) were all 99.99.

The same composition that was tested on the pathogens was tested for its film forming characteristics by dipping plastic disposable pipettes in the composition and allowing the composition on the dipped pipettes to dry. Identical pipettes were also dipped in two commercially available barrier teat dips. After drying, the pipettes were immersed in room temperature distilled water, and the time required for the film coating to be substantially lost, that is greater than 90% was determined. Similarly, the time to loss of the end drop on the pipettes, i.e., the point of thickest coating, was determined. As shown in the following table, the composition of the present invention formed an exceptionally durable film that was superior in performance to the two commercially available teat dips.

| TESTS FOR FILM FORMING CHARACTERISTICS | | | |
| --- | --- | --- | --- |
| | Composition of present invention | First commercial teat dip | Second commercial teat dip |
| Minutes to loss of film | 18 | 1 | 8 |
| Minutes to loss of end | 46 | 12 | 20 |

Although preferred embodiments of the germicidal, barrier forming composition of the present invention have been illustrated and described, it is to be understood that the present disclosure is made by way of example and that various other embodiments are possible without departing from the subject matter coming within the scope of the following claims, which subject matter is regarded as the invention.

What is claimed is:

1. An aqueous film forming teat sealing composition comprising:

from about 0.1% to about 5.0% by weight polyethylene glycol-lanolin complex; and from about 0.4% to about 20% amide condensation product of monoethanolamine and an organic acid having a carbon chain length of from 2 to 4.

2. The composition of claim 1 further containing an effective amount of a germicidal agent.

3. The composition of claim 1 further containing from about 0.05% to about 3.0% xanthan.

4. The composition of claim 3 further containing an effective amount of a germicidal agent.

5. The composition of claim 4 further containing an effective buffering agent to give the composition a pH of between about 5.3 and about 5.7.

6. The composition of claim 5 wherein the polyethylene glycol-lanolin complex, amide condensation product and xanthan are present in a ratio, by weight, of polyethylene glycol-lanolin complex to amide condensation product to xanthan of between about 1:4:1 and 2:20:1.

7. The composition of claim 6 wherein the ratio of polyethylene glycol-lanolin complex to amide condensation product to xanthan is about 1.5:6.2:1.

8. The composition of claim 6 wherein the germicidal agent is an iodine-nonionic surfactant complex that provides between about 0.1% and 2.5% by weight titratable iodine in the composition.

9. The composition of claim 6 wherein the germicidal agent is a water soluble iodine complex that provides between about 0.1% and 2.5% by weight of titratable iodine in the composition.

10. The composition of claim 9 wherein the polyethylene glycol-lanolin complex is polyethylene glycol 60 lanolin.

11. The composition of claim 10 wherein the amide condensation product is a condensation product of monoethanolamine and an acid selected from the group consisting of acetic acid, lactic acid and mixtures thereof.

12. The composition of claim 11 wherein the amide condensation produce is a condensation product of monoethanolamine and acetic acid.

13. The composition of claim 6 wherein the germicidal agent is a chlorhexidine salt selected from the group consisting of chlorhexidine digluconate, chlorhexidine diacetate, chlorhexidine diphosphate and mixtures thereof.

14. The composition of claim 13 wherein the clorhexidine salt is present in an amount of between about 0.1% and about 4.0% by weight.

15. The composition of claim 13 wherein the polyethylene glycol-lanolin complex is polyethylene glycol 60 lanolin.

16. The composition of claim 15 wherein the amide condensation product is a condensation product of monoethanolamine and an acid selected from the group consisting of acetic acid, lactic acid and mixtures thereof.

17. The composition of claim 16 wherein the amide condensation produce is a condensation product of monoethanolamine and acetic acid.

* * * * *